United States Patent [19]

McCurry, Jr. et al.

[11] Patent Number: 5,831,044

[45] Date of Patent: Nov. 3, 1998

[54] PROCESS FOR PREPARATION OF GLYCOSIDES

[75] Inventors: Patrick M. McCurry, Jr., Lansdale, Pa.; John Frederick Hessel, Metuchen, N.J.

[73] Assignee: Henkel Corporation, Plymouth Meeting, Pa.

[21] Appl. No.: 597,060

[22] Filed: Feb. 5, 1996

[51] Int. Cl.$^6$ .............................. C07H 15/04; C11D 3/22
[52] U.S. Cl. .................. 536/18.5; 536/4.1; 536/123.1; 536/123.13; 536/124; 510/470
[58] Field of Search ................... 536/18.5, 4.1, 536/123.1, 123.13, 124; 510/470

[56] References Cited

U.S. PATENT DOCUMENTS

| | | | |
|---|---|---|---|
| 3,565,885 | 2/1971 | Molotsky et al. | 260/210 |
| 3,839,318 | 10/1974 | Mansfield | 260/210 |
| 4,223,129 | 9/1980 | Roth et al. | 536/4 |
| 4,393,203 | 7/1983 | Mao et al. | 536/124 |
| 4,721,780 | 1/1988 | McDaniel, Jr. et al. | 536/18.6 |
| 4,939,245 | 7/1990 | Rasche et al. | 536/18.6 |
| 4,950,743 | 8/1990 | McCurry, Jr. et al. | 536/18.6 |
| 5,003,057 | 3/1991 | McCurry et al. | 536/186 |
| 5,079,350 | 1/1992 | Fujita et al. | 536/124 |
| 5,304,639 | 4/1994 | Gibson | 536/18.6 |
| 5,374,716 | 12/1994 | Biermann et al. | 536/18.6 |
| 5,478,930 | 12/1995 | McCurry, Jr. et al. | 536/18.6 |
| 5,494,659 | 2/1996 | Salka et al. | 424/70.13 |
| 5,519,124 | 5/1996 | McCurry, Jr. et al. | 536/18.5 |

Primary Examiner—John Kight
Assistant Examiner—Howard C. Lee
Attorney, Agent, or Firm—Ernest G. Szoke; Wayne C. Jaeschke; Steven J. Trzaska

[57] ABSTRACT

A process for making glycosides having enhance color properties comprising the steps of: (a) reacting a reducing saccharide with excess fatty alcohol to obtain a glycoside reaction mixture; (b) adding an effective amount of an unsaturated aliphatic carboxylic acid, including hydroxy-substituted derivatives thereof and their salt, to the glycoside reaction mixture; and (c) evaporating excess fatty alcohol from the glycoside reaction mixture to form a glycoside mixture.

20 Claims, No Drawings

PROCESS FOR PREPARATION OF GLYCOSIDES

BACKGROUND OF THE INVENTION

Glycoside surfactants have been known for at least sixty years. They are nonionic surfactants with low toxicity and gentleness to the skin. They can be made from renewable resources and are rapidly degraded in the environment.

In spite of the excellent properties of the glycoside surfactants, they have not achieved great commercial acceptance because of the difficulties encountered in their production. Rohm & Haas Corporation has been providing alkyl glycosides in which the alkyl group is formed from a mixture of fatty alcohols having 8 and 10 carbon atoms. The compositions are sold under the trade names BG-10 and CG-110. The BG-10 composition is a dark, almost black material and is used only in commercial formulations. The CG-110 material is a light colored mixture useful for consumer applications.

Early processes for the preparation of glycoside surfactants were two-step processes. The first step comprised the reaction of a lower alcohol having 1 to 6 carbon atoms with a saccharide source in the presence of an acid catalyst to form a alkyl glycoside. The glycosides prepared from the lower alcohols did not have useful surfactant properties. Since water is soluble in the alcohols, the reaction mixture could contain a substantial quantity of water (see U.S. Pat. No. 4,721,780). The higher glycoside surfactants in which the organic group attached to the glycoside moiety contains more than about 7 carbon atoms are then prepared by transacetalization of the lower glycoside with alcohols containing at least 7 carbon atoms under substantially anhydrous conditions.

More recently, aliphatic glycosides having aliphatic groups with from 7 to 22 carbon atoms have been prepared by a "direct process". In the "direct process" a long chain fatty alcohol is reacted with a source of saccharide in the presence of an acid catalyst under conditions in which the water formed in the reaction is removed as quickly as it is formed to maintain the water content of the reaction mixture at as low a level as is reasonably possible. The water formed in the reaction is only sparingly soluble in the fatty alcohol and any undissolved water results in the rapid formation of unwanted byproducts. The parameters of the "direct process" with a less than ideal catalyst and neutralization procedure are disclosed in U.S. Pat. No. 3,839,318, which is incorporated herein by reference. Other patents such as U.S. Pat. No. 4,939,245, U.S. Pat. No. 4,950,743 and U.S. Pat. No. 5,003,057 also disclose the "direct process" and are incorporated herein by reference.

The glycoside surfactants are formed by the reaction of the alcohol having more than about 7 carbon atoms and preferably more than about 8 carbon atoms with a saccharide source under anhydrous conditions in the presence of an acid catalyst. The reaction is generally carried out in the presence of a stoichiometric excess of the alcohol and at least a sufficient amount of alcohol to maintain the reaction mixture in a fluid state. Generally, the reaction mixture contains from about 1.5 to about 10 moles of alcohol per mole of saccharide moiety.

The reaction is carried out at a temperature in the range of from about 90° C. to about 145° C. under a reduced pressure. The high temperature and reduced pressure provide for rapid removal of the water formed in the reaction from the reaction mixture. The temperature and reduced pressure at which the reaction is carried out is dependent upon the alcohol used and the amount of discoloration which can be tolerated in the finished product. The lower molecular weight alcohols generally react at lower temperatures and at higher pressures, since at lower pressures the lower molecular weight alcohols tend to vaporize and change the composition of the reacting mixture.

After the source of saccharide has been substantially all reacted with the alcohols or polymerized to form a polymer, the acid catalyst is neutralized.

After the catalyst has been neutralized, it is generally accepted procedure that the unreacted or excess alcohol is then separated from the reaction mixture. Generally, it is desirable to have as low a content of the higher alcohol in the mixture as possible. The presence of higher alcohols are known to reduce the surfactant activity of the composition and to impact the odor of the product. Generally, the amount of alcohol remaining in the mixture is generally less than about 5% by weight of the mixture and preferably less than about 2% by weight and most preferably less than about 1.0% by weight of the product.

The alcohol is generally removed from the reaction mixture by heating the reaction mixture at a reduced pressure. Preferably, the alcohol is separated from the glycoside reaction mixture in a thin film evaporator such as disclosed in U.S. Pat. No. 4,223,129 or EP 077 167. U.S. Pat. No. 3,565,885 and U.S. Pat. No. 4,393,203 disclose that the most preferred method for removing the unreacted alcohol from the reaction mixture is in a wiped film evaporator. Especially with longer chain alcohols, a wiped film evaporator is particularly useful in that the glycoside reaction mixture is exposed to the high temperature for only a short period of time and the degradation caused by the vaporization process is substantially reduced.

U.S. Pat. No. 5,079,350 discloses that the most preferred method for removing unreacted alcohol from a glycoside surfactant mixture is to contact the alkyl glycoside and alcohol mixture with a stream of inert gas under reduced pressure in a wiped film evaporator maintained at a temperature in the range of about 140° C. to about 200° C. The process is disclosed as substantially removing all of the unreacted alcohol and the odor from the glycoside reaction mixture.

Wiped film evaporators have been recognized as being useful for removing high boiling point materials from heat sensitive products. However, wiped film evaporators are an expensive apparatus and have a limited surface area for a unit volume of the evaporator. It would be advantageous to be able to reduce the evaporation load which is required of the wiped film evaporator. The prior art teaches that the glycoside products are sensitive to heat and the color of the mixture deteriorates when the reaction mixture is exposed to a high temperature for a relatively long period of time. One skilled in the art faced with the problem of removing unreacted fatty alcohol from a glycoside mixture would select a process in which the glycoside mixture is exposed to an elevated temperature for as short a period of time as possible.

U.S. Pat. No. 5,304,639, incorporated herein by reference in its entirety, discloses that unreacted fatty alcohol can be readily removed from a reaction mixture containing a fatty alcohol and a fatty glycoside by first passing a mixture of fatty alcohol and fatty glycoside through an intermediate evaporation zone such as a falling film or forced circulation evaporation zone operated at a temperature in the range of about 140° C. to about 220° C. and a pressure in the range of from about 1.0 millimeters Hg to about 100 millimeters Hg to remove a portion of the alcohol from the fatty glycoside then passing the fatty glycoside with the reduced alcohol content from the forced circulation or falling film evaporation zone directly to a wiped film evaporation zone. Preferably the intermediate evaporation zone is a forced circulation evaporation zone.

The fatty glycoside entering the wiped film evaporation zone generally has a substantial portion of the fatty alcohol present in the original mixture removed and contains from about 10% by weight to about 60% by weight of fatty alcohol. The fatty alcohol content of the fatty glycoside is reduced in the wiped film evaporation zone to a range of less than about 5% by weight of the mixture of fatty alcohol and fatty glycoside and preferably less than about 2% by weight of the mixture and most preferably less than about 1.0% by weight of the mixture of alcohol and fatty glycoside.

While this method of removing alcohol may shorten the amount of time at which the glycoside reaction mixture is exposed to high temperatures, any length of exposure of the glycoside reaction mixture to elevated temperatures results in color degradation.

In an effort to rectify color degradation caused by exposure of the glycoside mixture to high evaporation temperatures, finishing chemicals such as alkali metal borohydride are used to treat the glycoside mixture in an effort to both reduce the color and to stabilize the color against deterioration over long periods of storage.

SUMMARY OF THE INVENTION

It has surprisingly been found that by adding an unsaturated aliphatic carboxylic acid, including salt derivatives thereof, to a glycoside reaction mixture, prior to initializing residual fatty alcohol evaporation procedures, the viscosity of the reaction mixture during the evaporation stage(s) is reduced, thereby resulting in lower evaporation temperatures being employed during the fatty alcohol evaporation stages. Lower evaporation temperatures result in less color degradation of the glycoside product.

Thus, the present invention provides a process for making glycoside products involving the steps of: (a) reacting a reducing saccharide with excess fatty alcohol to obtain a glycoside reaction mixture; (b) adding an effective amount of an unsaturated aliphatic carboxylic acid, including salt derivatives thereof to the glycoside reaction mixture; and (c) evaporating the excess fatty alcohol from the glycoside reaction mixture to form a glycoside product.

The present invention also provides a process for removing excess fatty alcohol from a glycoside reaction mixture involving the steps of: (a) reacting a reducing saccharide with excess fatty alcohol to obtain a glycoside reaction mixture; (b) adding an effective amount of an unsaturated aliphatic carboxylic acid, including salt derivatives thereof, to the glycoside reaction mixture; and (c) evaporating the excess fatty alcohol from the glycoside reaction mixture to form a glycoside product.

DESCRIPTION OF THE INVENTION

Other than in the operating examples, or where otherwise indicated, all numbers expressing quantities of ingredients or reaction conditions used herein are to be understood as being modified in all instances by the term "about".

The term "fatty alcohol" as used herein refers to alcohols having from 7 to about 22 carbon atoms. The alcohols can be saturated or unsaturated, straight chain or branched. The alcohols can contain saturated cyclic or unsaturated cyclic or aromatic moieties. Preferably, the fatty alcohol is an aliphatic alcohol having from 8 to about 18 carbon atoms and most preferably from about 8 to about 16 carbon atoms. Alcohols having aromatic or other cyclic moieties in their structure can also be reacted to form fatty glycoside products, but the fatty glycoside products are generally not as biodegradable as the fatty glycoside products formed from aliphatic alcohols.

The term "fatty glycoside" is used herein to denote a composition of the formula I:

$$RO(G)_n \qquad (I)$$

wherein R is a monovalent organic radical containing from about one to about 30 carbon atoms. Examples of such monovalent saturated aliphatic, unsaturated aliphatic or aromatic radicals include but are not limited to alkyl, hydroxyalkyl, alkenyl, hydroxyalkenyl, aryl, alkylaryl, hydroxyalkylaryl, arylalkyl, alkenylaryl, arylalkenyl, and the like. The preferred values of R are monovalent, saturated aliphatic groups which contain from 1 to about 18 carbon atoms and more preferably from 10 to about 18 carbon atoms. G represents a moiety derived from a reducing saccharide containing 5 or 6 carbon atoms and n is a number having an average value from 1 to about 6 and preferably from 1 to about 3 and most preferably from 1 to about 2. The preferred reducing saccharides are arabinose, xylose, glucose, galactose and combinations thereof.

The process according to the invention can be used in the production of derivatives of compounds of the formula I above including, for example, those in which one or more of the normally free (i.e., unreacted) hydroxyl groups of the saccharide moiety, G, have been alkoxylated, preferably, ethoxylated or propoxylated, so as to attach one or more pendant alkoxy or polyalkoxy groups in place thereof. In the case of the indicated alkoxylated derivatives, the amount of alkylene oxide, e.g., ethylene oxide, propylene oxide, employed will generally correspond to from about 1 to about 20 and preferably from about 3 to about 10 moles thereof per mole of saccharide moiety. Such derivatives have the formula II $$RO(R'O)_y(G)_n \qquad (II)$$

wherein R, G, and n are the same as those of formula I and wherein R' is a divalent hydrocarbon radical containing from 2 to about 4 carbon atoms and y is a number having an average value of from 1 to about 12.

Most preferably, the process according to the invention is best suited to the production of a fatty glycoside of the formula I as defined above and in particular wherein the reducing saccharide is glucose and the mixture produced is an alkyl polyglucoside.

The fatty glycoside can be formed by the two step process or the direct process since both processes produce reaction mixtures which contain unreacted fatty alcohol which must be removed from the fatty glycoside reaction mixture. However, the two step process reaction mixture generally contains some unreacted lower alcohol glycoside (1 to 6 carbon atoms) and some lower alcohol (1–6 carbon atoms) the lower alcohol must also be removed from the fatty glycoside reaction mixture.

After the alcohol has reacted with the source of saccharide to form the fatty glycoside, the reaction mixture is then neutralized (pH above about 7) and preferably the pH is increased to the range of about 9 to 12 and preferably between about 9.2 and about 10.5 The acid can be neutralized by contact with an alkali metal hydroxide or an alkali earth metal oxide or hydroxide or aluminum hydroxide or aluminum oxide. Preferably, the reaction mixture is neutralized with a mixture of alkali earth metal oxide and an alkali metal hydroxide. The presence of the alkali metal hydroxide is necessary to ensure that the pH of the mixture is maintained in a suitable range.

Generally, the neutralized reaction mixture contains from about 15% to about 50% by weight of the fatty glycoside mixture and from about 50% to about 85% by weight of unreacted fatty alcohol. The neutralized reaction mixture is then passed to a zone(s) wherein the unreacted fatty alcohol is separated from the fatty glycoside product.

As is known in the art, the fatty alcohol can be separated from the fatty glycoside reaction mixture by way of evaporation. The most commonly employed evaporating technique utilizes a thin film evaporation zone. However, it has been found that an even more efficient way for removing residual alcohol is by utilizing a two stage process. The first stage utilizes a forced circulation evaporation zone or falling film evaporation zone to remove a substantial portion of the unreacted fatty alcohol. The second stage involves passing the alkyl polyglycoside mixture with a reduced content of unreacted fatty alcohol to a wiped film evaporation zone to reduce the content of free fatty alcohol in the alkyl polyglycoside mixture to less than about 5% by weight, preferably less than about 2% by weight, and most preferably less than about 1.0% by weight of the mixture of fatty alcohol and alkyl polyglycoside product.

In the forced circulation evaporation zone, a reservoir of the reaction mixture having a portion of the fatty alcohol removed is maintained under a reduced pressure and at an elevated temperature. The pressure is generally in the range of from about 1.0 mm Hg to about 100 mm Hg and a temperature in the range of from about 120° C. to about 180° F. The mixture is pumped through a heat exchange means at a rate to maintain a velocity of from about 2 to about 25 feet per second in the heat exchanger and then introduced into the forced circulation evaporating zone vessel above a reservoir of the fatty glycoside with the reduced fatty alcohol content. The stream of material which has passed through the heat exchange means can be sprayed over the top of the reservoir or introduced tangentially at points along the sides of the vessel containing the reservoir of fatty glycoside mixture with the reduced content of fatty alcohol.

The heat exchange means of the forced circulation evaporating zone is operated at a pressure in the range of from about 0.1 mm to about 70 mm Hg, preferably less than 20 mm Hg and an evaporation temperature in the range of from about 140° C. to about 160° C., which is less than conventional evaporating temperatures. The liquid passing through the heat exchange means is maintained at a relatively high velocity to improve the heat transfer rate and reduce the difference in the temperature between the heating material and the circulating liquid to as low a value as practical. A restriction means such as a valve or an orifice is generally provided in the circulating system downstream of the heat exchange means to prevent boiling of the circulating liquid in the heat exchange means.

The neutralized reaction mixture which is introduced into the forced circulation evaporating zone can be introduced into the body of the liquid in the reservoir in the forced circulating evaporating vessel introduced into the suction or the discharge of the circulating pump so that the material is rapidly heated along with the circulating stream of the fatty glycoside mixture with the reduced fatty alcohol content.

The forced circulation evaporating zone can have mist elimination means to remove any materials which may tend to leave the forced circulation evaporation zone with the fatty alcohol vapors which are being separated from the fatty glycoside product. In addition, a stream of inert gas can be introduced into the reservoir of fatty glycoside mixture or into the vapor space above the reservoir of the fatty glycoside mixture to assist in reducing the content of fatty alcohol in the mixture. The forced circulating evaporating zone can be operated on a batch or a continuous basis. That is, the neutralized reaction mixture is introduced into the forced circulation evaporating zone and the reservoir of material circulated through the heat exchange means and returned to the reservoir of material in the forced circulating evaporating vessel until a composition with the desired content of fatty alcohol has been provided. At this point, a stream of the reaction mixture with reduced alcohol content is continuously introduced into the wiped film evaporation zone.

Preferably, the forced circulation evaporating zone is operated continuously wherein a stream of the neutralized reaction mixture is introduced continuously into the forced circulation evaporation zone and a stream of the forced evaporation zone mixture is introduced continuously into the wiped film evaporation zone.

Wiped film or thin film evaporators are well known in the art of separating high boiling point materials from heat sensitive products. In the wiped film evaporating zone, the feed comprising fatty alcohol and fatty glycoside is introduced into the input of the zone along the peripheral surface of the evaporator and a series of wiper blades rotating in the wiped film evaporation zone continuously wipe and spread the mixture over the heated surfaces of the wiped film evaporating zone. The heated surfaces of the wiped film evaporation zone can be heated by well known means such as hot oil, steam or even electrically as the case may require. The wiped film is continuously moved toward the discharge end of the wiped film evaporator by means of gravity if the evaporator is oriented vertically or by a pumping means if the evaporator is oriented horizontally.

The wiped film evaporation zone is generally operated at a temperature and pressure to provide a reactio mixture with the required fatty alcohol content. The temperature and pressure required in the wiped film evaporation zone is dependent upon the fatty alcohol which must be removed and the level of fatty alcohol permitted in the fatty glycoside reaction mixture. The wiped film evaporator is operated at a pressure in the range of from about 0.1 mm to about 70 mm Hg, preferably less than 20 mm Hg and an evaporation temperature in the range of from about 150° C. to about 220° C.

It should be noted, however, that the process of the present invention is not intended to be limited to only those evaporating techniques disclosed above. The present invention can employ either a forced circulation evaporating zone or a wiped film evaporating zone, and preferably employs both, i.e., evaporation in a forced circulation evaporating zone followed by further evaporation in a wiped film evaporating zone.

According to one aspect of the present invention, there is provided an improved process for making glycosides having reduced levels of decolorization. In this embodiment, an effective amount of an unsaturated carboxylic acid, including hydroxy-substituted derivatives thereof, and their salts, is added to the glycoside reaction mixture containing residual fatty alcohol to be evaporated therefrom, thereby reducing the viscosity of the glycoside reaction mixture during the evaporation stage(s). Residual fatty alcohol in the glycoside reaction mixture is then evaporated therefrom using an evaporating technique such as, for example, one of those disclosed above, at an evaporating temperature of from about 140° to about 195° C. It is because of the reduced viscosity of the glycoside reaction mixture during the evaporation stage(s), resulting from the introduction of the unsaturated carboxylic acid, including hydroxy-substituted derivatives thereof, and their salts, that significantly lower evaporating temperatures may be used during the removal of residual fatty alcohol. Lower evaporating temperatures result in reduced thermal degradation of the glycoside, which in turn reduces the degree of decolorization of the final glycoside product.

As was noted previously, because known alcohol distillation operations require temperatures in excess of 150° C, thermal degradation of the glycoside mixture normally takes place and produces an undesirable color in the product. The alcohol-free glycoside mixture is then normally subjected to one or more decolorization operations wherein the mixture is reacted with hydrogen peroxide or a Group I or Group II metal borohydride to remove any color bodies which may have been formed during the prior process steps such as the alcohol removal operation. However, by using the above-disclosed process for making glycosides, the use of decolorizing chemicals such as, for example, the alkali metal borohydrides listed above, to obtain a glycoside mixture of satisfactory color, is merely optional.

The amount of unsaturated carboxylic acid, including hydroxy-substituted derivatives thereof, and their salts, added to the glycoside reaction mixture prior to evaporation of excess fatty alcohol depends on the amount of glycoside reaction mixture to be subjected to the evaporation stage(s). Typically, it can range from about 0.1 to about 2.0 pounds acid/pound glycoside reaction mixture.

The unsaturated aliphatic carboxylic acids, including their hydroxy-substituted derivatives and salts thereof, employed in the present invention typically have from 6 to 22 carbon atoms. Preferred unsaturated fatty acids include: linoleic acid and its sodium or potassium salt (commercially available under the tradename EMERSOL® 315); linseed fatty acid (commercially available under the tradename EMERY® 643); or hydroxy-substituted unsaturated aliphatic carboxylic acids such as ricinoleic acid, and mixtures thereof.

Another aspect of the present invention provides for a process for removing excess fatty alcohol from a glycoside-containing reaction mixture involving adding an unsaturated carboxylic acid, including hydroxy-substituted derivatives thereof, and their salts, such as, for example, those disclosed above, to a glycoside reaction mixture containing residual fatty alcohol to be evaporated therefrom, thereby reducing both the viscosity of the glycoside reaction mixture during the evaporation stage(s) and temperature required for evaporation. The residual fatty alcohol in the glycoside reaction mixture is evaporated therefrom using an evaporating technique such as, for example, one of those disclosed above, at an evaporating temperature of from about 140° to about 195° C., which is less than the evaporating temperature employed in known processes for fatty alcohol removal.

As per above, the amount of unsaturated carboxylic acid, including hydroxy-substituted derivatives thereof, and their salts, added to the glycoside reaction mixture prior to evaporation of excess fatty alcohol depends on the amount of glycoside reaction mixture to be subjected to the evaporation stage(s). Typically, it can range from about 0.1 to about 2.0 pounds acid/pound glycoside reaction mixture.

What is claimed is:

1. A process for making alkyl glycosides having enhanced color properties comprising the steps of:
    (a) reacting a reducing saccharide with excess fatty alcohol to obtain a glycoside reaction mixture;
    (b) adding an effective amount of an unsaturated aliphatic carboxylic acid to reduce solution viscosity, including hydroxy-substituted derivatives thereof and their salts, to said glycoside reaction mixture; and
    (c) evaporating said excess fatty alcohol from said glycoside reaction mixture to form a alkyl glycoside product.

2. The process of claim 1 wherein said unsaturated aliphatic carboxylic acid is added to said glycoside reaction mixture in an amount ranging from about 0.1 to about 2.0 pounds of unsaturated aliphatic carboxylic acid/pound of glycoside reaction mixture.

3. The process of claim 1 wherein said unsaturated aliphatic carboxylic acid, including hydroxy-substituted derivatives thereof and their salts, have from 6 to 22 carbon atoms.

4. The process of claim 1 wherein said evaporating step is performed at an evaporation temperature of from about 140° to about 195° C.

5. The process of claim 1 wherein said evaporating step is performed using a forced circulation evaporating zone.

6. The process of claim 1 wherein said evaporating step is performed using a wiped film evaporating zone.

7. The process of claim 1 wherein said glycoside mixture is an alkyl polyglycoside.

8. The process of claim 1 wherein less than about 5% by weight excess fatty alcohol is contained in said glycoside product, based on the weight of the product.

9. The process of claim 5 wherein said evaporating step is performed using said forced circulation evaporating zone in combination with a wiped film evaporating zone.

10. The process of claim 1 further comprising treating said glycoside mixture of step (c) with an alkali metal borohydride.

11. A process for removing excess fatty alcohol from a alkyl glycoside reaction mixture comprising the steps of:
    (a) reacting a reducing saccharide with excess fatty alcohol to obtain a alkyl glycoside reaction mixture;
    (b) adding an effective amount of an unsaturated aliphatic carboxylic acid, including hydroxy-substituted derivatives thereof and their salt, to said alkyl glycoside reaction mixture; and
    (c) evaporating said excess fatty alcohol from said glycoside reaction mixture to form a alkyl glycoside product.

12. The process of claim 11 wherein said unsaturated aliphatic carboxylic acid, including hydroxy-substituted derivatives thereof and their salt, is added to said glycoside reaction mixture in an amount ranging from about 0.1 to about 2.0 pounds of unsaturated aliphatic carboxylic acid/pound of glycoside reaction mixture.

13. The process of claim 11 wherein said unsaturated aliphatic carboxylic acid, including hydroxy-substituted derivatives thereof and their salts have from 6 to 22 carbon atoms.

14. The process of claim 11 wherein said evaporating step is performed at an evaporation temperature of from about 140° to about 195° C.

15. The process of claim 11 wherein said evaporating step is performed using a forced circulation evaporating zone.

16. The process of claim 11 wherein said evaporating step is performed using a wiped film evaporating zone.

17. The process of claim 11 wherein said glycoside mixture is an alkyl polyglycoside.

18. The process of claim 11 wherein less than about 5% by weight excess fatty alcohol is contained in said glycoside product, based on the weight of the product.

19. The process of claim 15 wherein said evaporating step is performed using said forced circulation evaporating zone in combination with a wiped film evaporating zone.

20. The process of claim 11 further comprising treating said glycoside mixture of step (c) with an alkali metal borohydride.

* * * * *